(12) United States Patent
Tanaka et al.

(10) Patent No.: US 10,175,229 B2
(45) Date of Patent: Jan. 8, 2019

(54) RAPID METHOD FOR MEASURING CYTOTOXICITY IN NON-RI SYSTEM

(71) Applicant: NAGASAKI UNIVERSITY, Nagasaki-shi, Nagasaki (JP)

(72) Inventors: Yoshimasa Tanaka, Nagasaki (JP); Yuki Sakai, Nagasaki (JP); Satoshi Mizuta, Nagasaki (JP); Hiroshi Ueda, Nagasaki (JP)

(73) Assignee: NAGASAKI UNIVERSITY, Nagasaki (JP)

( * ) Notice: Subject to any disclaimer, the term of this patent is extended or adjusted under 35 U.S.C. 154(b) by 174 days.

(21) Appl. No.: 15/301,256

(22) PCT Filed: Mar. 30, 2015

(86) PCT No.: PCT/JP2015/059838
§ 371 (c)(1),
(2) Date: Sep. 30, 2016

(87) PCT Pub. No.: WO2015/152111
PCT Pub. Date: Oct. 8, 2015

(65) Prior Publication Data
US 2017/0016880 A1    Jan. 19, 2017

(30) Foreign Application Priority Data
Mar. 31, 2014  (JP) .................... 2014-073475

(51) Int. Cl.
| | | |
|---|---|---|
| *C07D 401/14* | (2006.01) | |
| *G01N 33/58* | (2006.01) | |
| *G01N 33/50* | (2006.01) | |
| *G01N 21/64* | (2006.01) | |
| *C07D 401/12* | (2006.01) | |
| *C07D 213/79* | (2006.01) | |

(52) U.S. Cl.
CPC ....... *G01N 33/5014* (2013.01); *C07D 213/79* (2013.01); *C07D 401/14* (2013.01); *G01N 21/6408* (2013.01); *G01N 33/5011* (2013.01); *G01N 33/582* (2013.01)

(58) Field of Classification Search
None
See application file for complete search history.

(56) References Cited

U.S. PATENT DOCUMENTS

| | | |
|---|---|---|
| 4,637,988 A | 1/1987 | Hinshaw et al. |
| 4,670,572 A | 6/1987 | Hinshaw et al. |
| 4,794,191 A | 12/1988 | Hinshaw et al. |
| 4,801,722 A | 1/1989 | Hinshaw et al. |
| 4,837,169 A | 6/1989 | Toner |
| 4,859,777 A | 8/1989 | Toner |
| 5,202,423 A | 4/1993 | Kankare et al. |
| 5,324,825 A | 6/1994 | Kankare et al. |
| 5,648,270 A | 7/1997 | Kuhn et al. |
| 6,013,802 A | 1/2000 | Hoyland et al. |
| 2012/0186396 A1 | 7/2012 | Marie et al. |

FOREIGN PATENT DOCUMENTS

| | | |
|---|---|---|
| EP | 0068875 A2 | 1/1983 |
| EP | 2161339 A1 | 3/2010 |
| JP | H03-500297 A | 1/1991 |
| WO | WO 1990/000550 A1 | 1/1990 |
| WO | WO 2011/009814 A1 | 1/2011 |

OTHER PUBLICATIONS

Blomberg et al., "Time-resolved fluorometric assay for natural killer activity using target cells labelled with a fluorescence enhancing ligand," *Journal of Immunological Methods*, 193(2): 199-206 (1996).
Hemmilä et al., "Di- and tetracarboxylate derivatives of pyridines, bipyridines and terpyridines as luminogenic reagents for time-resolved fluorometric determination of terbium and dysprosium," *Journal of Biochemical and Biophysical Methods*, 26(4): 283-290 (1993).
Japanese Patent Office, International Search Report in International Patent Application No. PCT/JP2015/059838 (dated Jun. 23, 2015) English translation.
European Patent Office, Extended European Search Report in European Patent Application No. 15773753.7 (dated Oct. 19, 2017).

*Primary Examiner* — Zinna Northington Davis
(74) *Attorney, Agent, or Firm* — Leydig, Voit & Mayer, Ltd.

(57) ABSTRACT

The present invention aims to provide a novel compound for measuring cellular cytotoxicity or cell proliferation capacity accurately with high reproducibility, conveniently and rapidly, and a measurement method of cellular cytotoxicity or cell proliferation capacity by using the compound. The present invention relates to a compound represented by the formula (I):

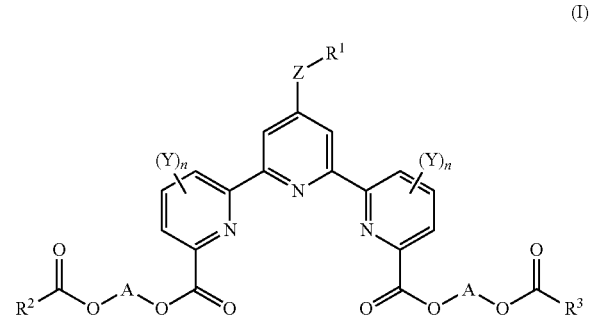

wherein $R^1$ is a substituent, $R^2$ and $R^3$ are each an optionally substituted hydrocarbon group, or an optionally substituted heterocyclic group, Y is a substituent, n is an integer of 0-3, Z is a single bond, —O—, —S—, —SO—, —SO$_2$—, or —NR$^4$— ($R^4$ is a hydrogen atom or a substituent), and A is an optionally substituted $C_{1-6}$ alkylene group) or a salt thereof.

16 Claims, 2 Drawing Sheets

Fig. 1 spontaneous release target cell: 100 µl
medium: 100 µl maximum release target cell: 100 µl
medium: 90 µl
0.125% digitonin solution: 10 µl effector cell/target cell ratio: HCT-4  K562

0
0.625
1.25
2.5
5
10
20
40 compound of Example 8
25 µM target cell: 100 µl
effector cell: 100 µl target cell: HCT-4 HTLV-1 infected cell
            K562 erythroblastoma
effector cell: helper NK cell

RAPID METHOD FOR MEASURING CYTOTOXICITY IN NON-RI SYSTEM

CROSS-REFERENCE TO RELATED APPLICATIONS

This patent application is the U.S. national phase of International Patent Application No. PCT/JP2015/059838, filed on Mar. 30, 2015, which claims the benefit of Japanese Patent Application No. 2014-073475, filed Mar. 31, 2014, the disclosures of which are incorporated herein by reference in their entireties for all purposes.

TECHNICAL FIELD

The present invention relates to a novel compound for measuring cellular cytotoxicity using non-RI, and a rapid measurement method of cellular cytotoxicity by using the compound.

BACKGROUND ART

In immunotherapy, immune cells such as NK cells, T cells and the like are taken out from plasma, expanded and/or activated ex vivo and administered to patients. At present, however, the effect varies even if the methodology is the same. The inconsistent effect may be attributable to the fact that immune cells insufficient in the expansion and/or activation are administered to patients, or the level of cytotoxicity of immune cells after expansion and/or activation is not measured in the process of the expansion and/or activation of immune cells. As a result, it is possible that the patients undergo a treatment, which may be ineffective, for a half year to one year or more.

As a method for measuring cell activity or viable cell number, a gamma ray measurement method using sodium chromate [51Cr] is known in the RI system, and release of lactic acid dehydrogenase and a time-resolved fluorometric method using terpyridine derivative chelate are known in the non-RI system (patent document 1, non-patent document 1). Since the gamma ray measurement method essentially requires use of RI facility capable of using gamma ray, it lacks broad utility and is difficult to adopt in the clinical site and the like. The lactic acid dehydrogenase-release assay has a problem of inaccurate measurement, since the background is too high due to a spontaneous release from effector cells in addition to the target cells. In addition, it is difficult to use the conventional Eu time-resolved fluorometric method using a terpyridine derivative chelate (e.g., bis(acetoxymethyl) 2,2':6',2"-terpyridine-6,6"-dicarboxylate: BATDA) as a standard measurement method, since release of chelate from the target cell is high and the results fluctuate widely depending on the cell condition.

DOCUMENT LIST

Patent Document patent document 1: National Publication of International Patent Application No. 3-500297

Non-Patent Document non-patent document 1: Journal of Immunological Methods, 193(2), 1996, pp. 199-206

SUMMARY OF THE INVENTION

Problems to be Solved by the Invention

The present invention aims to provide a novel compound for the measurement of cellular cytotoxicity with accuracy and reproducibility, and a convenient and rapid measurement method of cellular cytotoxicity by using the compound.

Means of Solving the Problems

The present inventors have conducted intensive studies in an attempt to solve the aforementioned problems and found that the cellular cytotoxicity can be measured conveniently with low spontaneous release and less fluctuation of values due to the cell state, by using a compound represented by the following formula (I), which resulted in the completion of the present invention.

Accordingly, the present invention is as described below.

[1] A compound represented by the formula (I):

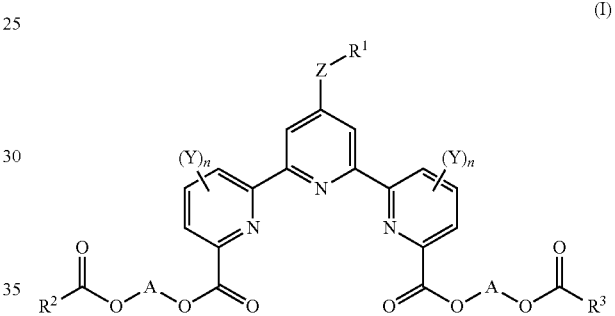

($R^1$ is a substituent,
$R^2$ and $R^3$ are each an optionally substituted hydrocarbon group, or an optionally substituted heterocyclic group,
Y is a substituent,
n is an integer of 0-3,
Z is a single bond, —O—, —S—, —SO—, —SO$_2$—, or —NR$^4$— ($R^4$ is a hydrogen atom or a substituent), and
A is an optionally substituted $C_{1-5}$ alkylene group),
or a salt thereof (hereinafter sometimes to be abbreviated as compound (I)).
[2] The compound of the above-mentioned [1], wherein A is methylene, or a salt thereof.
[3] An organic complex-forming agent comprising the compound of the above-mentioned [1] or [2], or a salt thereof.
[4] A reagent for viable cell number measurement comprising the compound of the above-mentioned [1] or [2], or a salt thereof.
[5] The reagent of the above-mentioned [4], which is a reagent for cellular cytotoxicity measurement.
[6] The reagent of the above-mentioned [4], which is a reagent for cell proliferation capacity measurement.
[7] A method of measuring cellular cytotoxicity, comprising a step of mixing the compound of the above-mentioned [1] or [2] or a salt thereof and a cell, and
a step of forming a complex with a lanthanoid element and measuring fluorescence.
[8] The method of the above-mentioned [7], wherein a surfactant is added before forming the complex with a lanthanoid element.

Effect of the Invention

The compound of the present invention which increases the polarity of the chelate compounds after intracellular degradation by esterases, by introducing a particular substituent into the terpyridine skeleton, is useful as a reagent for cellular cytotoxicity measurement or a reagent for cell proliferation measurement in the non-RI system, which are accurate, highly producibile and convenient. Since the measurement method of the present invention can determine cellular cytotoxicity or cell proliferation capacity of effector cells/target cells without using RI, conveniently and rapidly, it is useful for researches for cancer immunotherapy and virus infection, search for novel activation substance and the like in cell therapy, clinical tests and the like. Furthermore, the treatment effects can be enhanced by, during cell therapy, administering immune cells to patients after measuring the proliferative capacity and/or activation capacity thereof to confirm treatment effects.

BRIEF DESCRIPTION OF THE DRAWINGS

FIG. 1 shows the configuration of a 96-well plate in the cellular cytotoxicity measurement using the compound of the present invention (Example 8).

DESCRIPTION OF EMBODIMENTS

Figure 2:
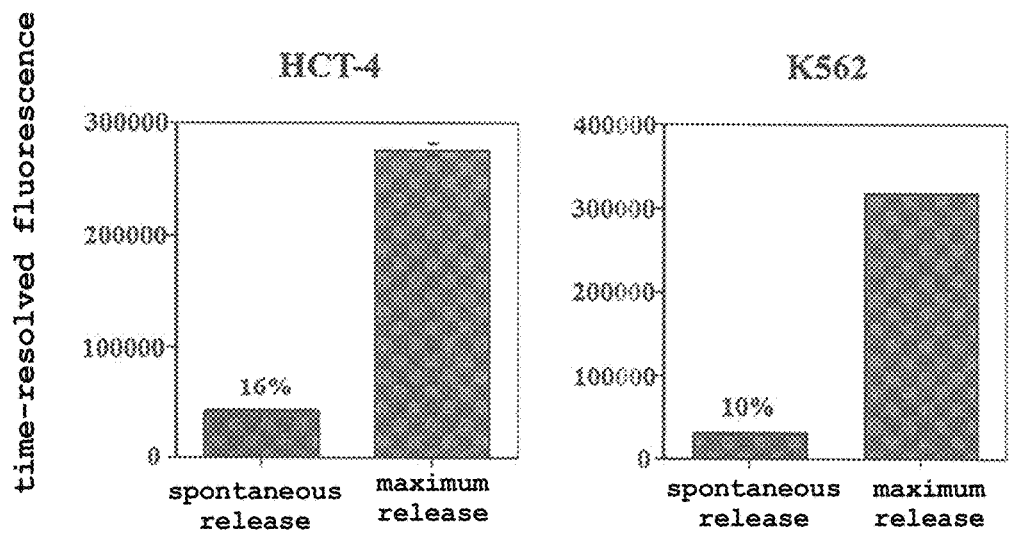
FIG. 2 shows the time-resolved fluorometric intensity of the virus infected cell HCT-4 and HCT-4 and the erythroblastoma K562 by using the compound of the present invention (Example 8).

The present invention is explained in detail in the following.

The definition of each substituent used in the present specification is described in detail in the following.

In the present specification, examples of the "halogen atom" include fluorine, chlorine, bromine and iodine.

As the "optionally substituted hydrocarbon group" in the present specification, unless otherwise specified, for example, "optionally substituted $C_{1-12}$ alkyl group", "optionally substituted $C_{2-12}$ alkenyl group", "optionally substituted $C_{2-12}$ alkynyl group", "optionally substituted $C_{3-8}$ cycloalkyl group", "optionally substituted $C_{3-8}$ cycloalkenyl group", "optionally substituted $C_{7-14}$ aralkyl group", "optionally substituted $C_{6-14}$ aryl group" and the like can be mentioned.

As the "$C_{1-12}$ alkyl (group)" in the present specification, unless otherwise specified, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl can be mentioned. As the "$C_{1-6}$ alkyl (group)" in the present specification, a "$C_{1-12}$ alkyl (group)" having 1-6 carbon atoms can be mentioned.

As the "$C_{2-12}$ alkenyl (group)" in the present specification, unless otherwise specified, for example, vinyl, propenyl, isopropenyl, 2-buten-1-yl, 4-penten-1-yl, 5-hexen-1-yl and the like can be mentioned. As the "$C_{2-6}$ alkenyl (group)" in the present specification, the above-mentioned "$C_{2-12}$ alkenyl (group)" having 2-6 carbon atoms can be mentioned.

As the "$C_{2-12}$ alkynyl (group)" in the present specification, unless otherwise specified, for example, 2-butyn-1-yl, 4-pentyn-1-yl, 5-hexin-1-yl and the like can be mentioned. As the "$C_{2-6}$ alkynyl (group)" in the present specification, the above-mentioned "$C_{2-12}$ alkynyl (group)" having 2-6 carbon atoms can be mentioned.

As the "$C_{3-8}$ cycloalkyl (group)" in the present specification, unless otherwise specified, for example, cyclopropyl, cyclobutyl, cyclopentyl, cyclohexyl, cycloheptyl, cyclobutyl and the like can be mentioned.

As the "$C_{3-8}$ cycloalkenyl (group)" in the present specification, unless otherwise specified, for example, cyclopropenyl (e.g., 2-cyclopropen-1-yl), cyclobutenyl (e.g., 2-cyclobuten-1-yl), cyclopentenyl (e.g., 1-cyclopenten-1-yl, 2-cyclopenten-1-yl, 3-cyclopenten-1-yl), cyclohexenyl (e.g., 1-cyclohexen-1-yl, 2-cyclohexen-1-yl, 3-cyclohexen-1-yl) and the like can be mentioned.

As the "$C_{7-14}$ aralkyl (group)" in the present specification, unless otherwise specified, for example, benzyl, phenethyl, 1-methyl-2-phenylethyl, diphenylmethyl, 1-naphthylmethyl, 2-naphthylmethyl, 2,2-diphenylethyl, 3-phenylpropyl, 4-phenylbutyl, 5-phenylpentyl and the like can be mentioned.

As the "$C_{6-14}$ aryl (group)" in the present specification, unless otherwise specified, for example, phenyl, 1-naphthyl, 2-naphthyl, 1-anthryl, 2-anthryl, 9-anthryl can be mentioned.

As the "$C_{1-12}$ alkoxy (group)" in the present specification, unless otherwise specified, for example, methoxy, ethoxy, propoxy, isopropoxy, butoxy, isobutoxy, sec-butoxy, tert-butoxy, pentyloxy, hexyloxy, heptyloxy, octyloxy, nonyloxy, decyloxy, undecyloxy, dodecyloxy can be mentioned. As the "$C_{1-6}$ alkoxy (group)", a "$C_{1-12}$ alkoxy (group)" having 1-6 carbon atoms can be mentioned.

As the "$C_{2-12}$ alkenyloxy (group)" in the present specification, unless otherwise specified, for example, vinyloxy, propenyloxy, isopropenyloxy and the like can be mentioned. As the "$C_{2-6}$ alkenyloxy (group)", a "$C_{2-12}$ alkenyloxy (group)" having 2-6 carbon atoms can be mentioned.

As the "$C_{2-12}$ alkynyloxy (group)" in the present specification, unless otherwise specified, for example, 2-butynyloxy, 2-pentynyloxy, 5-hexynyloxy and the like can be mentioned. As the "$C_{2-6}$ alkynyloxy (group)", a "$C_{2-12}$ alkynyloxy (group)" having 2-6 carbon atoms can be mentioned.

As the "$C_{3-8}$ cycloalkyloxy (group)" in the present specification, unless otherwise specified, for example, cyclopropyloxy, cyclobutyloxy, cyclopentyloxy, cyclohexyloxy, cycloheptyloxy, cyclooctyloxy and the like can be mentioned.

As the "$C_{3-8}$ cycloalkenyloxy (group)" in the present specification, unless otherwise specified, for example, cyclopropenyloxy (e.g., 2-cyclopropenyloxy), cyclobutenyloxy (e.g., 2-cyclobutenyloxy), cyclopentenyloxy (e.g., 1-cyclopentenyloxy, 2-cyclopentenyloxy, 3-cyclopentenyloxy), cyclohexenyloxy (e.g., 1-cyclohexenyloxy, 2-cyclohexenyloxy, 3-cyclohexenyloxy) and the like can be mentioned.

As the "$C_{7-14}$ aralkyloxy (group)" in the present specification, unless otherwise specified, for example, benzyloxy, phenethyloxy and the like can be mentioned.

As the "$C_{6-14}$ aryloxy (group)" in the present specification, unless otherwise specified, for example, phenoxy, 1-naphthyloxy, 2-naphthyloxy and the like can be mentioned.

As the "heterocyclyl-oxy (group)" in the present specification, a hydroxy group substituted by the below-mentioned "heterocycle (group)" can be mentioned. As preferable examples of the heterocyclyl-oxy (group), tetrahydropyranyloxy, thiazolyloxy, pyridyloxy, pyrazolyloxy, oxazolyloxy, thienyloxy, furyloxy and the like can be mentioned.

As the "$C_{1-6}$ alkylsulfanyl (group)" in the present specification, unless otherwise specified, for example, methylsulfanyl, ethylsulfanyl, propylsulfanyl, isopropylsulfanyl, butylsulfanyl, sec-butylsulfanyl, tert-butylsulfanyl and the like can be mentioned.

As the "$C_{2-6}$ alkenylsulfanyl (group)" in the present specification, unless otherwise specified, for example, vinylsulfanyl, propenylsulfanyl, isopropenylsulfanyl and the like can be mentioned.

As the "$C_{1-6}$ alkylsulfonyl (group)" in the present specification, unless otherwise specified, for example, methylsulfonyl, ethylsulfonyl, propylsulfonyl, isopropylsulfonyl, butylsulfonyl, sec-butylsulfonyl, tert-butylsulfonyl and the like can be mentioned.

As the "$C_{1-6}$ alkylene group" in the present specification, methylene, ethylene, propylene, butylene, pentylene, hexylene can be mentioned.

As the "heterocycle(group)" in the present specification, unless otherwise specified, for example, a 3- to 14-membered (monocyclic, bicyclic or tricyclic) heterocyclic group containing, as a ring-constituting atom besides carbon atom, one or two kinds of 1 to 4 hetero atoms selected from nitrogen atom, sulfur atom and oxygen atom, preferably, (i) a 5- to 14-membered (preferably, 5- to 10-membered) aromatic heterocyclic group, (ii) a 3- to 8-membered nonaromatic heterocyclic group and the like can be mentioned. Of these, a 5- or 6-membered aromatic heterocyclic group, or a 5- or 6-membered nonaromatic heterocyclic group is preferable. Specifically, for example, aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazolopyridinyl (e.g., pyrazolo[1,5-a]pyridin-3-yl) and the like; nonaromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydrofuryl, tetrahydropyranyl and the like, and the like can be mentioned.

As the "optionally substituted $C_{1-12}$ alkyl group", "optionally substituted $C_{2-12}$ alkenyl group", "optionally substituted $C_{2-12}$ alkynyl group", "optionally substituted $C_{1-6}$ alkylene group" in the present specification, "$C_{1-12}$ alkyl group", "$C_{2-12}$ alkenyl group", "$C_{2-12}$ alkynyl group", "$C_{1-6}$ alkylene group", each optionally having 1 to 5 substituents selected from

[Substituent Group A]
(1) halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-6}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N—$C_{1-6}$ alkyl-N—$C_{6-14}$ aryl-amino;
(11) N—$C_{1-6}$ alkyl-N—$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxyl;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N—$C_{1-6}$ alkyl-N—$C_{6-14}$ aryl-carbamoyl;
(26) mono- or di-5- to 7-membered heterocyclyl-carbamoyl;
(27) $C_{1-6}$ alkyl-carbonylamino optionally substituted by carboxyl;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{5-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{5-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(35) $C_{1-6}$ alkyl-carbonyloxy;
(36) $C_{1-6}$ alkoxy-carbonyl;
(37) mono- or di-$C_{1-6}$ alkyl-carbonylamino;
(38) mono- or di-$C_{1-6}$ alkoxy-carbonylamino;
(39) mono- or di-$C_{6-14}$ aryloxy-carbonylamino;
(40) mono- or di-$C_{7-14}$ aralkyloxy-carbonylamino;
(41) tri-$C_{1-6}$ alkylsilyloxy;
and the like at substitutable position(s) can be mentioned. When plural substituents are present, the respective substituents may be the same or different.

As the "optionally substituted $C_{3-8}$ cycloalkyl group", "optionally substituted $C_{3-8}$ cycloalkenyl group", "optionally substituted $C_{7-14}$ aralkyl group", "optionally substituted $C_{6-14}$ aryl group", "optionally substituted heterocyclic group" in the present specification, "$C_{3-9}$ cycloalkyl group", "$C_{3-8}$ cycloalkenyl group", "$C_{7-14}$ aralkyl group", "$C_{6-14}$ aryl group", "heterocyclic group", each optionally having 1 to 5 substituents selected from
[Substituent Group B]
(1) substituent group A;
(2) optionally substituted $C_{1-6}$ alkyl;
(3) optionally substituted $C_{2-6}$ alkenyl;
(4) optionally substituted $C_{2-6}$ alkynyl;
and the like, at substitutable position(s), can be mentioned. When plural substituents are present, the respective substituents may be the same or different.

In substituent group B, as the substituent of the "optionally substituted $C_{1-6}$ alkyl", "optionally substituted $C_{2-6}$ alkenyl", "optionally substituted $C_{2-6}$ alkynyl group", a substituent selected from the above-mentioned substituent group A can be mentioned. The number of the substituents is 1-substitutable maximum number, more preferably 1-3.

The definition of each substituent used in the formula (I) is described in detail in the following.

$R^1$ is a substituent.
$R^1$ is preferably an optionally substituted $C_{1-12}$ alkyl group, or an optionally substituted $C_{1-12}$ alkoxy group.
$R^1$ is more preferably $C_{1-6}$ alkyl (e.g., methyl, ethyl, propyl) optionally substituted by 1 to 3 substituents selected from
(1) a hydroxy group,
(2) a formyl group,
(3) a $C_{1-6}$ alkyl-aminocarbonyl group (e.g., ethylaminocarbonyl),
and
(4) a hydroxy-$C_{1-6}$ alkoxy group (e.g., hydroxyethoxy).

$R^2$ and $R^3$ are each an optionally substituted hydrocarbon group, or an optionally substituted heterocyclic group.
$R^2$ and $R^3$ are preferably $C_{1-12}$ alkyl groups.
$R^2$ and $R^3$ are more preferably $C_{1-6}$ alkyl groups (e.g., methyl, ethyl, propyl).
Y is a substituent.
n is an integer of 0-3.
n is preferably 0.
Z is a single bond, —O—, —S—, —SO—, —SO$_2$—, or —NR$^4$— (R$^4$ is a hydrogen atom or a substituent).
Z is preferably a single bond or —O—.
A is an optionally substituted $C_{1-6}$ alkylene group.
A is preferably methylene.

Preferable examples of the group, substituent and the like explained in the present specification are more preferably used in combination.

As preferable compound (I), the following compounds can be mentioned.

[Compound A]
A compound wherein $R^1$ is $C_{1-6}$ alkyl (e.g., methyl, ethyl, propyl) optionally substituted by 1 to 3 substituents selected from
(1) a hydroxy group,
(2) a formyl group,
(3) a $C_{1-6}$ alkyl-aminocarbonyl group (e.g., ethylaminocarbonyl),
and
(4) a hydroxy-$C_{1-6}$ alkoxy group (e.g., hydroxyethoxy),
$R^2$ and $R^3$ are $C_{1-6}$ alkyl groups (e.g., methyl, ethyl, propyl),
n is 0,
Z is a single bond or —O—, and
A is a methylene group,
or a salt thereof.

Specific examples of the above-mentioned compound (I) include the compounds of Examples 1-9.

Of compounds (I), examples of the salt include metal salt, ammonium salt, salts with organic bases, salts with inorganic acids, salts with organic acids and the like. Preferable examples of the metal salt include alkali metal salts such as sodium salt, potassium salt and the like; alkaline earth metal salts such as calcium salt, magnesium salt, barium salt and the like; aluminum salt and the like. Preferable examples of the salts with organic bases include salts with trimethylamine, triethylamine, pyridine, ethanolamine, diethanolamine, triethanolamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

The production method of the compound (I) of the present invention or a salt thereof is now explained.

While a production intermediate obtained in the following production method can also be used for the next reaction without purification, it may be used after isolation and purification from the reaction mixture by a known method such as chromatography, recrystallization and the like.

The compound (I) of the present invention can be produced, for example, by the following Method A and Method B.

In compound (I), a compound represented by the formula (Ia) or a salt thereof wherein $R^1$ is an alkoxy group (hereinafter to be also referred to as compound (Ia)) can be produced by the following Method A or a method analogous thereto.

[Method A]

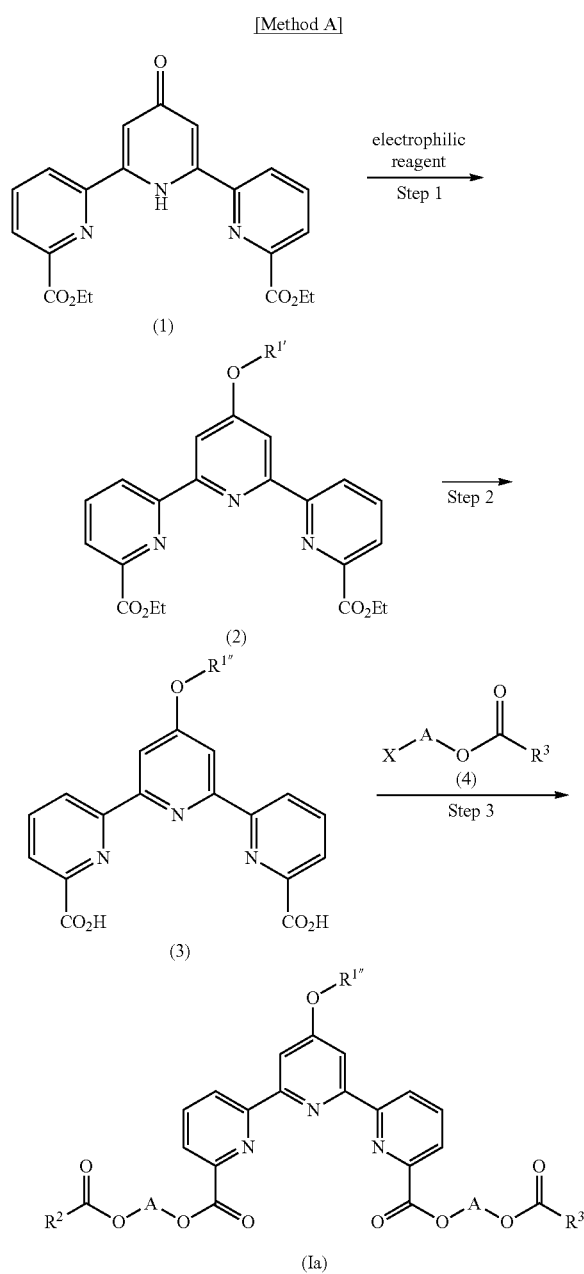

wherein $R^{1'}$ and $R^{1'''}$ are each an optionally substituted $C_{1-12}$ alkyl group, X is a halogen atom, A is as defined above, and $R^2$ and $R^3$ are as defined above and the same, and X is preferably a chlorine atom.

(Step 1)

Diethyl 1',H-[2,2':6',2'']terpyridine-4'-oxo-6,6''-dicarboxylate (hereinafter to be also referred to as compound (1)) is added to alkali metal hydride, and the mixture is reacted with an electrophilic reagent to produce 0-substituted-2,2':6',2''-terpyridine-6,6''-dicarboxylate (hereinafter to be also referred to as compound (2)).

Compound 1 can be produced by a known method (P. Kadjane, C. Plata-Iglesias, R. Ziessel, L. J. Charbonniere, Dalton Trans. 2009, 5688-5700) or a method analogous thereto.

Examples of the alkali metal hydride include sodium hydride, potassium hydride and the like.

Examples of the electrophilic reagent include methyl iodide, ethyl bromide and the like.

The amount of the electrophilic reagent to be used is generally about 1-3 mol, preferably about 1-2 mol, per 1 mol of compound (1).

This step is performed in a solvent that does not adversely influence the reaction.

Examples of the solvent that does not adversely influence the reaction include dimethylformamide, THF, diethyl ether and the like.

The reaction temperature is generally about 0-100° C., preferably about 20-50° C.

The reaction time is generally about 2-48 hr, preferably about 12-24 hr.

(Step 2)

A mixture of compound (2) and a base is stirred, and the pH of the reaction mixture is adjusted with an acid to produce 4'-substituted-2,2':6',2''-terpyridine-6,6''-dicarboxylic acid (hereinafter to be also referred to as compound (3)).

Examples of the base include sodium hydroxide, potassium hydroxide, lithium hydroxide and the like.

The amount of the base to be used is generally about 2-10 mol, preferably about 3-5 mol, per 1 mol of compound (2).

Examples of the acid include hydrochloric acid, acetic acid.

The pH is generally about 2-5, preferably about 3-4.

The reaction temperature is generally about 0-100° C., preferably about 20-40° C.

The reaction time is generally about 10-48 hr, preferably about 12-36 hr.

(Step 3)

Compound (3) is reacted with a haloalkylalkoxylate derivative represented by the formula (4) (hereinafter to be also referred to as compound (4)) in the presence of a base to produce compound (Ia).

Examples of the base include triethylamine, diisopropylethylamine, N,N-dimethyl-4-aminopyridine and the like.

The amount of the base to be used is generally about 2-10 mol, preferably about 2-4 mol, per 1 mol of compound (3).

Compound (4) to be used may be a commercially available product, or can also be produced from the corresponding starting compound by a known method.

The amount of compound (4) to be used is generally about 2-6 mol, preferably about 2-4 mol, per 1 mol of compound (3).

This step is performed in a solvent that does not adversely influence the reaction.

Examples of the solvent that does not adversely influence the reaction include dimethylformamide, THF and the like.

The reaction temperature is generally about 0-100° C., preferably about 40-60° C.

The reaction time is generally about 12-48 hr, preferably about 12-36 hr.

Compound (1), compound (2) and compound (3) obtained by the above-mentioned Method A can also be further derivatized by subjecting to various known reactions such as acylation reaction, alkylation reaction, amidation reaction, oxidation reaction, reduction reaction, hydrolysis, dehydration reaction and the like. Such reaction can be performed by a method known per se or according thereto.

When compound (1), compound (2) and compound (3) have a functional group such as a hydroxy group and the like, the reaction can be performed with appropriate protection. Such protecting group and protection•deprotection can be performed according to known protecting groups and methods (e.g., Wiley-Interscience, "Protective Groups in Organic Synthesis, 3rd Ed." 1999 (Theodora W. Greene, Peter G. M. Wuts)).

In compounds (I), a compound represented by the formula (Ib) or a salt thereof wherein $R^1$ is a hydroxymethyl group (hereinafter to be also referred to as compound (Ib)) can be produced by the following Method B or a method analogous thereto.

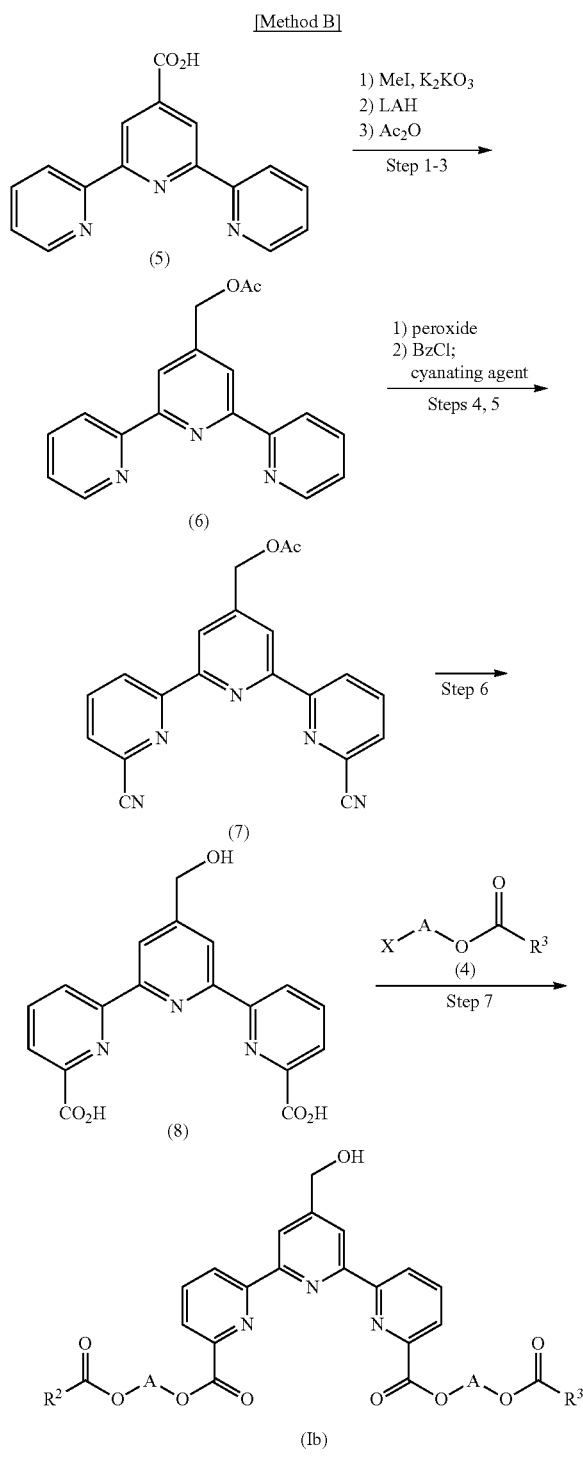

wherein A and X are as defined above, and $R^2$ and $R^3$ are as defined above and the same, and X is preferably a chlorine atom.

(Step 1)

2,2':6',2"-Terpyridine-4'-carboxylic acid represented by the formula (5) (hereinafter to be also referred to as compound (5)), potassium carbonate and methyl iodide are reacted to produce a methylester form of compound (5).

The amount of potassium carbonate to be used is generally about 1-5 mol, preferably about 2-3 mol, per 1 mol of compound (5).

The amount of methyl iodide to be used is generally about 1-5 mol, preferably about 1-2 mol, per 1 mol of compound (5).

This step is performed in a solvent that does not adversely influence the reaction.

Examples of the solvent that does not adversely influence the reaction include dimethylformamide, THF and the like.

The reaction temperature is generally about 0-100° C., preferably about 20-40° C.

The reaction time is generally about 2-48 hr, preferably about 12-24 hr.

(Step 2)

The methylester form of compound (5) is reduced with lithium aluminum hydride to produce a hydroxymethyl form of compound (5).

The amount of lithium aluminum hydride to be used is generally about 1-3 mol, preferably about 1-2 mol, per 1 mol of compound (5).

This step is performed in a solvent that does not adversely influence the reaction.

Examples of the solvent that does not adversely influence the reaction include THF, diethyl ether and the like.

The reaction temperature is generally about −20-50° C., preferably about 0-20° C.

The reaction time is generally about 1-12 hr, preferably about 3-5 hr.

(Step 3)

The hydroxymethyl form of compound (5) is dissolved in pyridine and reacted with acetic anhydride to produce 2,2': 6',2"-terpyridin-4'-ylmethyl acetate represented by the formula (6) (hereinafter to be also referred to as compound (6)).

The amount of pyridine to be used is generally about 1-10 L, preferably about 2-5 L, per 1 mol of compound (5).

The amount of acetic anhydride to be used is generally about 1-10 mol, preferably about 1-2 mol, per 1 mol of compound (5).

The reaction temperature is generally about 0-100° C., preferably about 20-40° C.

The reaction time is generally about 2-48 hr, preferably about 12-24 hr.

(Step 4)

Compound (6) is reacted with peroxide to produce pyridineoxide of compound (6).

This step is performed in a solvent that does not adversely influence the reaction.

Examples of the solvent that does not adversely influence the reaction include dichloromethane, chloroform, carbon tetrachloride, 1,2-dichloroethane, chlorobenzene and the like.

The reaction temperature is generally about −20-50° C., preferably about 0-20° C.

The reaction time is generally about 2-48 hr, preferably about 12-24 hr.

(Step 5)

The pyridineoxide of compound (6) is reacted with benzoylchloride and then with a cyanating agent to produce (6, 6"-dicyano-2,2':6',2"-terpyridin-4'-yl)methyl acetate represented by the formula (7) (hereinafter to be also referred to as compound (7)).

This step is performed in a solvent that does not adversely influence the reaction.

Examples of the solvent that does not adversely influence the reaction include dichloromethane and the like.

The amount of benzoylchloride to be used is generally 2-10 mol, preferably about 4-5 mol, per 1 mol of compound (6).

Examples of the cyanating agent include trimethylsilyl cyanide and the like.

The amount of the cyanating agent to be used is generally 2-10 mol, preferably about 4-5 mol, per 1 mol of compound (6).

The reaction temperature is generally about 0-100° C., preferably about 20-40° C.

The reaction time is generally about 2-48 hr, preferably about 12-24 hr.

(Step 6)

Compound (7) is subjected to alkali hydrolysis to produce 4'-(hydroxymethyl)-2,2':6',2"-terpyridine-6,6"-dicarboxylic acid represented by the formula (8) (hereinafter to be also referred to as compound (8)).

This step can be performed similarly to Step 2 of the above-mentioned Method A.

(Step 7)

Compound (8) is reacted with compound (4) in the presence of a base to produce compound (Ib).

This step can be performed similarly to Step 3 of the above-mentioned Method A.

The compound of the present invention can form, after intracellular degradation by esterase, an organic complex with a lanthanoid element, and the viable cell number can be measured by measuring the fluorescence of the complex. What can be measured by the compound of the present invention is not limited to the viable cell number and, for example, cellular cytotoxicity and cell proliferation capacity can be mentioned.

The measurement method of cellular cytotoxicity of the present invention is now explained.

The method of the present invention includes a step of mixing a compound represented by the formula (I) and the cell, and a step of forming a complex with a lanthanoid element and measuring the fluorescence.

The "cell" in the method of the present invention is a cell having cellular cytotoxicity and, for example, immunocytes such as NK cell, T cell and the like, cancer cells such as leukemia cell and the like, and the like can be mentioned.

Examples of the "lanthanoid element" in the method of the present invention include europium, samarium, terbium and the like. Preferably, europium is used.

The "surfactant" in the method of the present invention is appropriately selected from NP-40, Triton X-100, digitonin, CHAPS and the like. Preferred is digitonin.

The above-mentioned fluorescence can be measured, for example, by time-resolved fluorometric measurement.

Since the method for measuring cellular cytotoxicity of the present invention has higher sensitivity as compared to conventional cellular cytotoxicity assays, the measurement time can be shortened.

When cellular cytotoxicity is measured in the present invention, a spontaneous release amount of a labeled compound needs to be examined, as a method therefor, for example, the following method can be mentioned.

1. The target cell is incubated in RPMI1640 medium overnight at 37° C., 5% $CO_2$.

2. The cells are seeded in RPMI1640 medium at a concentration of $1\times10^6$ cells/mL, a compound represented by the formula (I) is added at a final concentration of 25 μM, and the cells are incubated at 37° C., 5% $CO_2$ for 15 min.

3. A 0.125% digitonin DMSO solution prepared when in use is added, mixed well, and the cells are incubated at 37° C., 5% $CO_2$ for 15 min.

The digitonin DMSO solution is prepared by dissolving digitonin in DMSO, immediately adding water to adjust the final digitonin concentration to 0.0625%.

4. After mixing well and centrifugation, the supernatant is transferred to a plate (96-well, flat bottom) containing an Eu solution (250 μL).

5. After standing for 15 min, the time-resolved fluorescence is measured by a PHERA star microplate reader.

EXAMPLES

The present invention is explained further specifically by the following Examples, which are not to be construed as limitative.

All NMR data were measured by Gemini300 (Varian Inc.), AL 400 (JEOL Inc.), and 500PS spectroscope (Varian Inc.). 1H and 13C NMR spectra are shown as chemical shift (δ) in parts per million (ppm) relative to the solvent peak by using tetramethylsilane or (2,2,3,3-D4)trimethylsilyl-3-propionic acid or a sodium salt (1H and 13C) as the internal standard. The chemical shift (δ) is indicated in parts per million (ppm), and the coupling constant (J) is indicated in hertz (Hz) unit. To describe multiplicity, the following abbreviations are used.

s=singlet, d=doublet, t=triplet, q=quartet, quint.=quintet, sext.=sextet, sept.=septet, br=broad, m=multiplet All reactions were performed by stirring with a magnetic stirrer and under an inert gas atmosphere. Flash column chromatography was performed using silica gel C60 (50-200 μm) manufactured by Fuji Silysia Chemical Ltd. or CHROMATOREX DIOL (MB 100-40/75) and using an eluate system as described in the section of Experiments. TLC was performed using TLC Silic gel 60 F254 aluminum sheets (Merck Inc.) or silica gel F254 glass plates (Merck Inc.).

The meaning of the abbreviations in the Examples is as described below.

NMR: nuclear magnetic resonance spectrum

Hz: hertz

J: coupling constant

HRMS: High Resolution Mass Spectrometer

THF: tetrahydrofuran

DMF: N,N-dimethylformamide

DMSO: dimethyl sulfoxide

DIEA: diisopropylethylamine

IPE: diisopropyl ether

TEA: triethylamine

BATDA: bis(acetoxymethyl) 2,2':6',2"-terpyridine-6,6"-dicarboxylate

Example 1 bis(butyryloxymethyl) 4'-(2-hydroxyethoxy)-2,2':6', 2''-terpyridine-6,6''-dicarboxylate (Step 1)

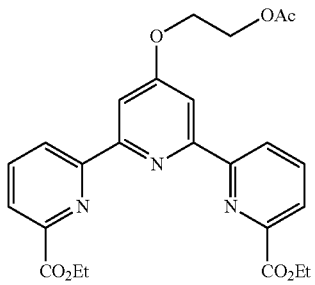 [SMILES: CCOC(=O)c1cccc(-c2cc(OCCOC(C)=O)cc(-c3cccc(C(=O)OCC)n3)n2)n1]

According to the method described in the above-mentioned Method A, step 1 (2.5 mmol scale), and using 2-acetoxyethylbromide as an electrophilic reagent, the reaction was performed. The obtained crude product was purified by flash column chromatography (eluent: 50% n-hexane/ethyl acetate) to give diethyl 4'-(2-acetoxyethoxy)-2,2':6',2''-terpyridine-6,6''-dicarboxylate (494 mg, yield 41%) as an orange solid.

$^1$H NMR (500 MHz, CDCl$_3$) δ 1.48 (t, J=7.1 Hz, 6H), 2.14 (s, 3H), 4.49-4.54 (m, 4H), 4.52 (q, J=7.1 Hz, 4H), 8.00 (t, J=7.8 Hz, 2H), 8.16 (dd, J=1.0, 7.6 Hz, 2H), 8.20 (s, 2H), 8.80 (dd, J=1.0, 7.8 Hz, 2H); $^{13}$C NMR (125 MHz, CDCl$_3$) δ 14.3, 20.9, 61.8, 62.4, 66.1, 108.3, 124.3, 125.1, 137.7, 147.8, 156.0, 156.4, 165.2, 166.8, 170.9.

(Step 2)

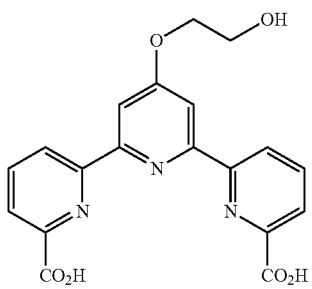 [SMILES: O=C(O)c1cccc(-c2cc(OCCO)cc(-c3cccc(C(=O)O)n3)n2)n1]

According to the method described in the above-mentioned Method A, step 2 (0.8 mmol scale), and using diethyl 4'-(2-acetoxyethoxy)-2,2':6',2''-terpyridine-6,6''-dicarboxylate, the reaction was performed. The obtained crude product was concentrated under reduced pressure to give 4'-(2-hydroxyethoxy)-2,2':6',2''-terpyridine-6,6''-dicarboxylic acid (248 mg, yield 78%) as a yellow solid. The obtained solid was used for the next reaction without further purification.

$^1$H NMR (500 MHz, d-DMSO) δ 3.84 (t, J=4.6 Hz, 2H), 4.32 (t, J=4.6 Hz, 2H), 8.16 (d, J=7.1 Hz, 2H), 8.19 (t, J=7.8 Hz, 2H), 8.24 (s, 2H), 8.84 (d, J=7.6 Hz, 2H); $^{13}$C NMR (125 MHz, d-DMSO) δ 59.4, 70.2, 107.9, 123.6, 124.8, 138.7, 154.3, 155.9, 166.3, 167.3.

(Step 3)

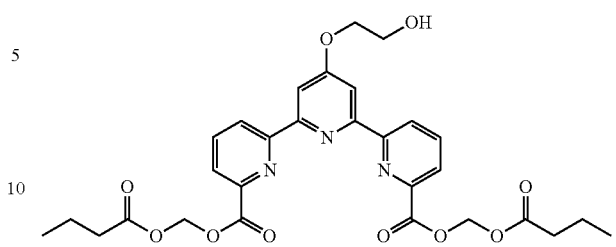

According to the method described in the above-mentioned Method A, step 3 (0.39 mmol scale), and using 4'-(2-hydroxyethoxy)-2,2':6',2''-terpyridine-6,6''-dicarboxylic acid and butyryloxymethylchloride, the reaction was performed. The obtained crude product was purified by flash column chromatography (eluent: 50% n-hexane/ethyl acetate) to give bis(butyryloxymethyl) 4'-(2-hydroxyethoxy)-2,2':6',2''-terpyridine-6,6''-dicarboxylate (101 mg, yield 45%) as a yellow solid.

$^1$H NMR (500 MHz, CDCl$_3$) δ 0.97 (t, J=7.4 Hz, 6H), 1.70 (sext. J=7.6 Hz, 4H), 2.41 (t, J=7.4 Hz, 4H), 4.08 (t, J=4.4 Hz, 2H), 4.41 (t, J=4.9 Hz, 2H), 6.11 (s, 4H), 7.99 (t, J=7.8 Hz, 2H), 8.16 (dd, J=1.2, 7.6 Hz, 2H), 8.18 (s, 2H), 8.78 (dd, J=1.0, 7.9 Hz, 2H); $^{13}$C NMR (125 MHz, CDCl$_3$) δ 13.5, 18.1, 35.8, 61.1, 69.6, 80.1, 108.5, 124.9, 125.6, 137.8, 146.3, 156.0, 156.2, 163.9, 167.1, 172.3.

Example 2 bis(acetoxymethyl) 4'-(2-oxo-2-(propylamino)ethoxy)-2,2':6',2''-terpyridine-6,6''-dicarboxylate (Step 1)

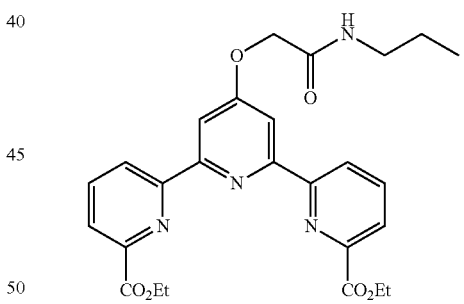

According to the method described in the above-mentioned Method A, step 1 (1.0 mmol scale), and using 2-oxo-2-(propylamino)ethoxymethylbromide as an electrophilic reagent, the reaction was performed. The obtained crude product was purified by flash column chromatography (eluent: 50% n-hexane/ethyl acetate) to give diethyl 4'-(2-oxo-2-(propylamino)ethoxy)-2,2':6',2''-terpyridine-6,6''-dicarboxylate (342 mg, yield 70%) as a white solid.

$^1$H NMR (500 MHz, CDCl$_3$) δ 0.99 (t, J=7.1 Hz, 3H), 1.50 (t, J=7.4 Hz, 6H), 1.65 (sext. J=7.3 Hz. 2H), 3.38 (q, J=7.9 Hz, 2H), 4.53 (t, J=7.1 Hz, 4H), 6.76 (br. t, NH), 8.01 (t, J=7.9 Hz, 2H), 8.17 (dd, J=1.0, 7.6 Hz, 2H), 8.22 (s, 2H), 8.79 (dd, J=1.0, 7.9 Hz, 2H); $^{13}$C NMR (125 MHz, CDCl$_3$) δ 11.3, 14.3, 22.8, 40.9, 61.9, 66.8, 108.2, 124.3, 125.3, 137.8, 147.8, 155.6, 156.7, 165.1, 165.3, 166.9.

(Step 2)

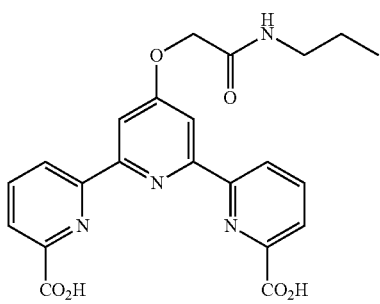 [SMILES: CCCNC(=O)COc1cc(-c2cccc(C(=O)O)n2)nc(-c2cccc(C(=O)O)n2)c1]

According to the method described in the above-mentioned Method A, step 2 (0.6 mmol scale), and using diethyl 4'-(2-oxo-2-(propylamino)ethoxy)-2,2':6',2"-terpyridine-6,6"-dicarboxylate, the reaction was performed, whereby 4'-(2-oxo-2-(propylamino)ethoxy)-2,2':6',2"-terpyridine-6,6"-dicarboxylic acid (210 mg, yield 79%) was obtained as a pale-yellow solid.

$^1$H NMR (500 MHz, d-DMSO) δ 0.84 (t, J=7.6 Hz, 3H), 1.48 (sext. J=7.1 Hz, 2H), 3.13 (q, J=6.4 Hz, 2H), 4.82 (s, 2H), 8.15 (dd, J=1.2, 7.8 Hz, 2H), 8.20 (t, J=7.9 Hz, 2H), 8.25 (s, 2H), 8.37 (br. t, J=5.9 Hz, NH), 8.86 (dd, J=1.2, 7.8 Hz, 2H); $^{13}$C NMR (125 MHz, d-DMSO) δ 11.4, 22.4, 40.2, 66.9, 108.1, 124.2, 125.2, 138.9, 147.9, 154.6, 155.8, 165.9, 166.2, 166.6.

(Step 3)

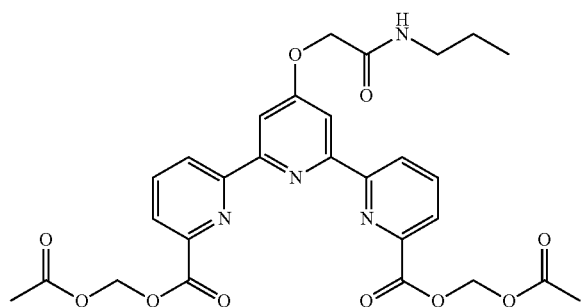 [SMILES: CCCNC(=O)COc1cc(-c2cccc(C(=O)OCOC(C)=O)n2)nc(-c2cccc(C(=O)OCOC(C)=O)n2)c1]

According to the method described in the above-mentioned Method A, step 3 (0.14 mmol scale), and using 4'-(2-oxo-2-(propylamino)ethoxy)-2,2':6',2"-terpyridine-6,6"-dicarboxylic acid and acetoxymethylchloride, the reaction was performed. The obtained crude product was purified by column chromatography to give bis(acetoxymethyl) 4'-(2-oxo-2-(propylamino)ethoxy)-2,2':6',2"-terpyridine-6,6"-dicarboxylate (78 mg, yield 98%) as a white solid.

$^1$H NMR (500 MHz, CDCl$_3$) δ 1.00 (t, J=7.6 Hz, 3H), 1.67 (sext, J=7.4 Hz, 2H), 2.19 (s, 6H), 3.40 (q, J=7.3 Hz, 2H), 4.79 (s, 2H), 6.11 (s, 4H), 6.78 (br. t, J=5.6 Hz, NH), 8.03 (t, J=7.9 Hz, 2H), 8.20 (d, J=7.4 Hz, 2H), 8.22 (s, 2H), 8.82 (d, J=7.6 Hz, 2H); $^{13}$C NMR (125 MHz, CDCl$_3$) δ 11.4, 20.8, 22.8, 40.9, 66.9, 80.3, 108.4, 125.0, 125.9, 138.0, 146.5, 155.9, 156.5, 163.8, 165.4, 166.8, 169.6.

Example 3 bis(acetoxymethyl) 4'-(2-hydroxyethoxy)-2,2':6',2"-terpyridine-6,6"-dicarboxylate (Step 1)

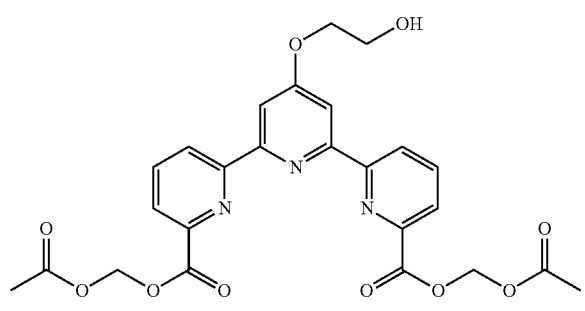 [SMILES: CC(=O)OCOC(=O)c1cccc(-c2cc(OCCO)cc(-c3cccc(C(=O)OCOC(C)=O)n3)n2)n1]

According to the method described in the above-mentioned Method A, step 3 (0.05 mmol scale), and using 4'-(2-hydroxyethoxy)-2,2':6',2"-terpyridine-6,6"-dicarboxylic acid and acetoxymethylchloride, the reaction was performed. The obtained crude product was purified by preparative TLC (eluent: chloroform:acetone=4:1) to give the title compound (12 mg, yield 47%) as a white solid.

$^1$H NMR (500 MHz, CDCl$_3$) δ 2.18 (s, 6H), 4.07-4.10 (m, 2H), 4.42 (t, J=4.5 Hz, 2H), 6.11 (s, 4H), 8.01 (t, J=8.0 Hz, 2H), 8.18 (d, J=8.0 Hz, 2H), 8.21 (s, 2H), 8.81 (d, J=8.0 Hz, 2H); $^{13}$C NMR (125 MHz, CDCl$_3$) δ 20.8, 61.1, 65.6, 80.2, 108.5, 124.9, 125.7, 137.9, 146.4, 156.1, 156.3, 163.9, 165.5, 169.6.

Example 4 bis(butyryloxymethyl) 4'-(2-oxyethoxy)-2,2':6',2"-terpyridine-6,6"-dicarboxylate (Step 1)

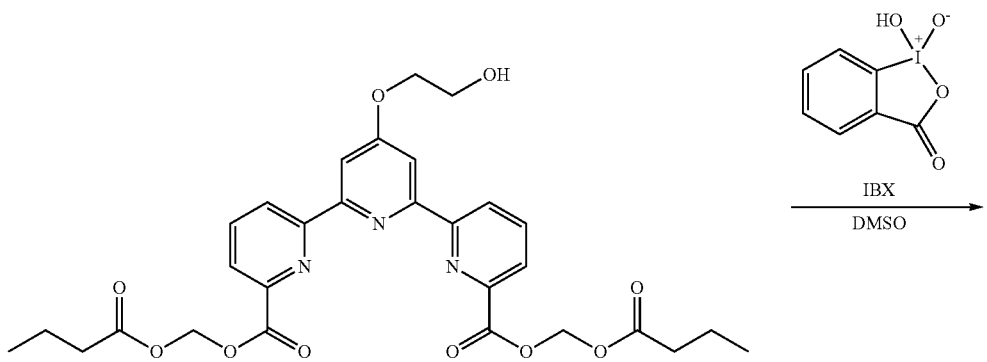

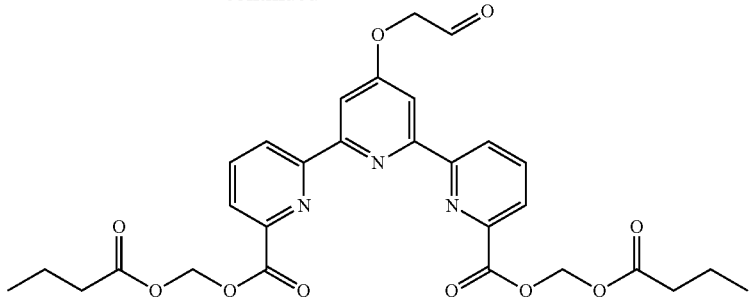

To a suspension of 2-iodoxybenzoic acid (60 mg, 0.21 mmol) in DMSO (2 mL) was added bis(butyryloxymethyl) 4'-(2-hydroxyethoxy)-2,2':6',2"-terpyridine-6,6"-dicarboxylate (25 mg, 0.04 mmol) at room temperature, and the mixture was stirred for 24 hr. The reaction was quenched with water, the organic layer was separated, and the aqueous layer was extracted with ethyl acetate (2×10 mL). The organic layer was combined, washed with brine and dried over magnesium sulfate. After filtration, the filtrate was concentrated under reduced pressure. The obtained crude product was purified by silica gel column chromatography (eluent: ethyl acetate) to give the title compound (19 mg, yield 74%) as a white solid.

$^1$H NMR (500 MHz, CDCl$_3$) δ 0.98 (t, J=7.4 Hz, 6H), 1.71 (sext. J=7.3 Hz, 4H), 2.42 (t, J=7.6 Hz, 4H), 4.93 (s, 2H), 6.12 (s, 4H), 8.02 (t, J=8.1 Hz, 2H), 8.18-8.21 (m, 4H), 8.81 (d, J=7.8 Hz, 2H), 9.96 (s, 1H); $^{13}$C NMR (125 MHz, CDCl$_3$) δ 13.5, 18.1, 35.8, 72.4, 80.1, 108.3, 124.9, 125.8, 137.9, 146.4, 163.8, 172.3, 172.5, 197.0.

Example 5 bis(propionyloxymethyl) 4'-(2-hydroxyethoxy)-2,2': 6',2"-terpyridine-6,6"-dicarboxylate (Step 1)

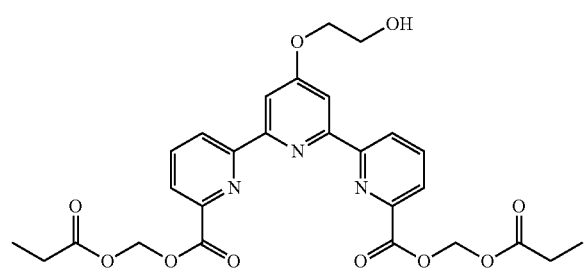 [SMILES: CCC(=O)OCOC(=O)c1cccc(-c2cc(OCCO)cc(-c3cccc(C(=O)OCOC(=O)CC)n3)n2)n1]

According to the method described in the above-mentioned Method A, step 3 (0.05 mmol scale), and using 4'-(2-hydroxyethoxy)-2,2':6',2"-terpyridine-6,6"-dicarboxylic acid and propionyloxymethylchloride, the reaction was performed. The obtained crude product was purified by preparative TLC (eluent: chloroform:acetone=2:1) to give the title compound (4 mg, yield 13%) as a white solid.

$^1$H NMR (500 MHz, CDCl$_3$) δ 1.19 (t, J=8.0 Hz, 6H), 2.46 (q, J=8.0 Hz, 4H), 4.07-4.10 (m, 2H), 4.41 (t, J=4.5 Hz, 2H), 6.12 (s, 4H), 8.01 (t, J=7.5 Hz, 2H), 8.18 (dd, J=1.0, 7.5 Hz, 2H), 8.21 (s, 2H), 8.82 (dd, J=1.0, 7.5 Hz, 2H).

Example 6 bis(butyryloxymethyl) 4'-(3-hydroxypropoxy)-2,2': 6',2"-terpyridine-6,6"-dicarboxylate (Step 1)

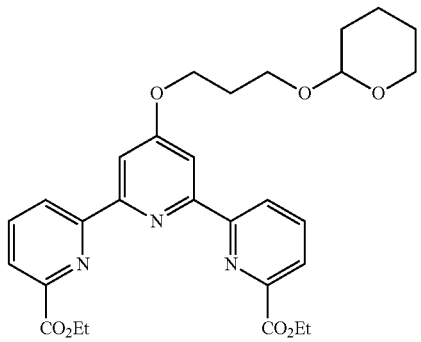 [SMILES: CCOC(=O)c1cccc(-c2cc(OCCCOC3CCCCO3)cc(-c3cccc(C(=O)OCC)n3)n2)n1]

According to the method described in the above-mentioned Method A, step 1 (0.5 mmol scale), and using 3-((tetrahydro-2H-pyran-2-yl)oxy)propylbromide as an electrophilic reagent, the reaction was performed. The obtained crude product was purified by flash column chromatography (eluent: hexane:ethyl acetate=2:1-1:1) to give diethyl 4'-(3-((tetrahydro-2H-pyran-2-yl)oxy)propoxy)-2,2': 6',2"-terpyridine-6,6"-dicarboxylate (110 mg, yield 40%) as a white solid.

$^1$H NMR (500 MHz, CDCl$_3$) δ 1.49 (t, J=7.0 Hz, 6H), 1.52-1.63 (m, 4H), 1.70-1.76 (m, 1H), 1.80-1.89 (m, 1H), 2.18 (quint., J=6.0 Hz, 2H), 3.50-3.54 (m, 1H), 3.63-3.67 (m, 1H), 3.85-3.90 (m, 1H), 3.98-4.02 (m, 1H), 4.37-4.44 (m, 2H), 4.51 (q, J=7.0 Hz, 4H), 4.63 (t, J=4.5 Hz, 1H), 7.98 (t, J=8.0 Hz, 2H), 8.14 (dd, J=1.0, 8.0 Hz, 2H), 8.17 (s, 2H), 8.78 (dd, J=1.0, 8.0 Hz, 2H); $^{13}$C NMR (125 MHz, CDCl$_3$) δ 14.3, 19.6, 25.4, 29.5, 30.6, 61.8, 62.3, 63.7, 65.2, 99.0, 108.3, 124.3, 125.0, 137.6, 147.7, 156.2, 156.2, 165.3, 167.3.

(Step 2)

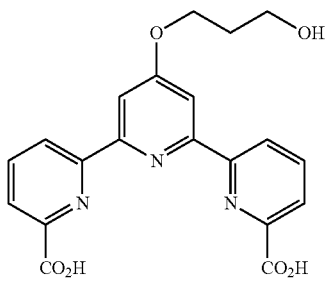 [SMILES: O=C(O)c1cccc(-c2cc(OCCCO)cc(-c3cccc(C(=O)O)n3)n2)n1]

According to the method described in the above-mentioned Method A, step 2 (0.20 mmol scale), and using diethyl 4'-(3-((tetrahydro-2H-pyran-2-yl)oxy)propoxy)-2,2':6',2"-terpyridine-6,6"-dicarboxylate, the reaction was performed, whereby 4'-(3-hydroxypropoxy)-2,2':6',2"-terpyridine-6,6"-dicarboxylic acid (61 mg, yield 77%) as a yellow solid. The obtained solid was used for the next reaction without further purification.

$^1$H NMR (500 MHz, d-DMSO) δ 1.93-1.99 (m, 2H), 3.62 (t, J=6.0 Hz, 2H), 4.33 (t, J=6.0 Hz, 2H), 8.11-8.19 (m, 6H), 8.78-8.84 (m, 2H); $^{13}$C NMR (125 MHz, d-DMSO) δ 32.0, 57.2, 65.6, 108.0, 124.3, 125.3, 139.0, 147.9, 154.6, 155.6, 165.9, 167.4.

(Step 3)

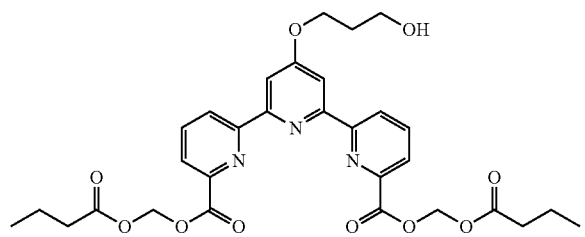 [SMILES: CCCC(=O)OCOC(=O)c1cccc(-c2cc(OCCCO)cc(-c3cccc(C(=O)OCOC(=O)CCC)n3)n2)n1]

According to the method described in the above-mentioned Method A, step 3 (0.05 mmol scale), and using 4'-(3-hydroxypropoxy)-2,2':6',2"-terpyridine-6,6"-dicarboxylic acid and butyryloxymethylchloride, the reaction was performed. The obtained crude product was purified by preparative TLC (eluent: hexane:ethyl acetate=2:1) to give bis(butyryloxymethyl) 4'-(3-hydroxypropoxy)-2,2':6',2"-terpyridine-6,6"-dicarboxylate (15 mg, yield 51%) as a white solid.

$^1$H NMR (500 MHz, CDCl$_3$) δ 0.98 (t, J=7.5 Hz, 6H), 1.71 (sext., J=7.5 Hz, 4H), 2.16 (quint., J=6.0 Hz, 2H), 2.41 (t, J=7.5 Hz, 4H), 3.93 (t, J=6.0 Hz, 2H), 4.46 (t, J=6.0 Hz, 2H), 6.11 (s, 4H), 8.01 (t, J=8.0 Hz, 2H), 8.17 (d, J=8.0 Hz, 2H), 8.22 (s, 2H), 8.81 (d, J=8.0 Hz, 2H); $^{13}$C NMR (125 MHz, CDCl$_3$) δ 13.5, 18.1, 31.9, 35.8, 59.6, 65.7, 80.1, 108.6, 124.9, 125.6, 137.8, 146.4, 156.1, 156.4, 163.9, 167.3, 172.4.

Example 7 bis(butyryloxymethyl) 4'-(2-(2-hydroxyethoxy)ethoxy)-2,2':6',2"-terpyridine-6,6"-dicarboxylate (Step 1)

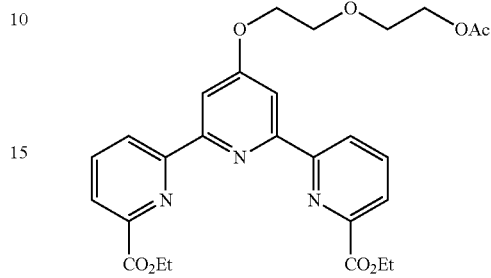

According to the method described in the above-mentioned Method A, step 1 (1.3 mmol scale), and using 2-(2-acetoxyethoxy)ethylbromide as an electrophilic reagent, the reaction was performed. The obtained crude product was purified by flash column chromatography (eluent: 50% n-hexane/ethyl acetate) to give diethyl 4'-(2-(2-acetoxyethoxy)ethoxy)-2,2':6',2"-terpyridine-6,6"-dicarboxylate (60 mg, yield 9%) as an orange solid.

$^1$H NMR (400 MHz, CDCl$_3$) δ 1.49 (t, J=7.1 Hz, 6H), 2.08 (s, 3H), 3.81-3.83 (m, 2H), 3.96-3.98 (m, 2H), 4.27 (t, J=3.5 Hz, 2H), 4.43-4.46 (m, 2H), 4.50 (q, J=7.1 Hz, 4H), 7.98 (t, J=7.6 Hz, 2H), 8.13 (d, J=7.6 Hz, 2H), 8.19 (s, 2H), 8.87 (d, J=7.8 Hz, 2H); $^{13}$C NMR (125 MHz, CDCl$_3$) δ 14.2, 20.8, 61.8, 63.5, 67.6, 69.3, 108.4, 124.4, 125.1, 137.7, 147.8, 156.2, 156.4, 165.4, 167.1, 171.1.

(Step 2)

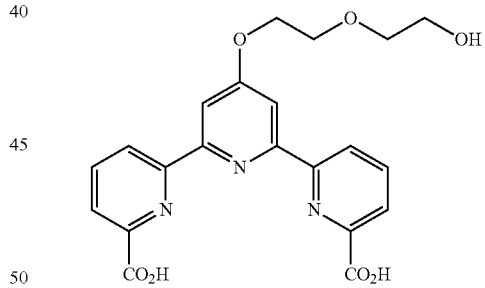

According to the method described in the above-mentioned Method A, step 2 (0.1 mmol scale), and using diethyl 4'-(2-(2-acetoxyethoxy)ethoxy)-2,2':6',2"-terpyridine-6,6"-dicarboxylate, the reaction was performed and the mixture was concentrated under reduced pressure to give 4'-(2-(2-hydroxyethoxy)ethoxy)-2,2':6',2"-terpyridine-6,6"-dicarboxylic acid (30 mg, yield>90%) as a white solid. The obtained solid was used for the next reaction without further purification.

$^1$H NMR (500 MHz, d-DMSO) δ 3.55 (m, 4H), 3.87 (t, J=4.2 Hz, 2H), 4.44 (t, J=3.9 Hz, 2H), 8.15 (dt, J=1.3, 7.6 Hz, 2H), 8.20 (t, J=7.6 Hz, 2H), 8.26 (d, J=1.7 Hz, 2H), 8.86 (ddd, J=1.3, 2.4, 7.8 Hz, 2H); $^{13}$C NMR (125 MHz, d-DMSO) δ 60.7, 68.4, 69.1, 73.0, 108.5, 124.7, 125.6, 139.4, 148.2, 166.3, 167.5.

(Step 3)

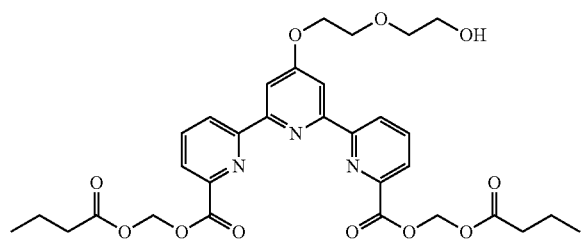 [SMILES: CCCC(=O)OCOC(=O)c1cccc(-c2cc(OCCOCCO)cc(-c3cccc(C(=O)OCOC(=O)CCC)n3)n2)n1]

According to the method described in the above-mentioned Method A, step 3 (0.07 mmol scale), and using 4'-(2-(2-hydroxyethoxy)ethoxy)-2,2':6',2"-terpyridine-6,6"-dicarboxylic acid and butyryloxymethylchloride, the reaction was performed. The obtained crude product was purified by flash column chromatography (eluent: ethyl acetate) to give bis(butyryloxymethyl) 4'-(2-(2-hydroxyethoxy)ethoxy)-2,2':6',2"-terpyridine-6,6"-dicarboxylate (21 mg, yield 56%) as a pale-yellow solid.

$^1$H NMR (500 MHz, CDCl$_3$) δ 0.98 (t, J=7.6 Hz, 6H), 1.71 (sext. J=7.6 Hz, 4H), 2.41 (t, J=7.3 Hz, 4H), 3.72 (dd, J=3.9, 5.6 Hz, 2H), 3.80 (dd, J=4.2, 4.9 Hz, 2H), 3.97-3.99 (m, 2H), 4.47-4.49 (m, 2H), 6.11 (s, 4H), 8.00 (t, J=7.6 Hz, 2H), 8.17 (dd, J=1.0, 7.8 Hz, 2H), 8.24 (s, 2H), 8.81 (dd, J=1.0, 7.8 Hz, 2H); $^{13}$C NMR (125 MHz, CDCl$_3$) δ 13.5, 18.1, 35.8, 61.2, 67.7, 69.6, 72.7, 80.1, 108.7. 124.9, 125.6, 137.8, 146.4, 156.0, 156.4, 163.9, 167.2, 172.3.

Example 8 bis(butyryloxymethyl) 4'-(hydroxymethyl)-2,2':6',2"-terpyridine-6,6"-dicarboxylate (Step 1)

To a solution of 2,2':6',2"-terpyridine-4'-carboxylic acid (200 mg, 0.72 mmol) in DMF (3.6 mL) were added potassium carbonate (20 mg, 1.4 mmol) and methyl iodide (0.07 mL, 1.1 mmol), and the reaction mixture was stirred at room temperature for 16 hr. To the reaction mixture was added brine, and the aqueous layer was extracted with ethyl acetate (3×5.0 mL), and the extract was washed with brine, and dried over magnesium sulfate. The mixture was filtered, and concentrated under reduced pressure to give a crude product. The obtained crude product was used for the next reaction without purification. To a solution of the crude product (0.72 mmol) in tetrahydrofuran (7.2 mL) was added lithium aluminum hydride (28 mg, 0.7 mmol) at 0° C. After stirring for 3 hr, sodium sulfate 10 hydrate was added to the reaction mixture, and the mixture was stirred at room temperature for 1 hr. The reaction mixture was filtered through a celite pad, and the filtrate was concentrated under reduced pressure. The residue was dissolved in pyridine (3.6 mL), and acetic anhydride (0.14 mL, 1.4 mmol) was added to the solution. After stirring for 16 hr, toluene was added to the mixture, and concentrated under reduced pressure. The residue was purified by CHROMATOREX Diol silica gel column chromatography (eluent: n-hexane:ethyl acetate=1:0-1:1) to give 2,2':6',2"-terpyridine-4'-ylmethyl acetate (88 mg, yield 40% 3 steps) as a white solid.

$^1$H NMR (500 MHz, CDCl$_3$) δ 2.20 (s, 3H), 5.28 (s, 2H), 7.32-7.35 (m, 2H), 7.85 (dt, J=2.0, 8.0 Hz, 2H), 8.43 (s, 2H), 8.61 (td, J=1.0, 8.0 Hz, 2H), 8.70-8.71 (m, 2H); $^{13}$C NMR (125 MHz, CDCl$_3$) δ 20.9, 64.8, 119.2, 121.3, 123.9, 136.8, 146.9, 149.1, 155.8, 155.8, 170.6.

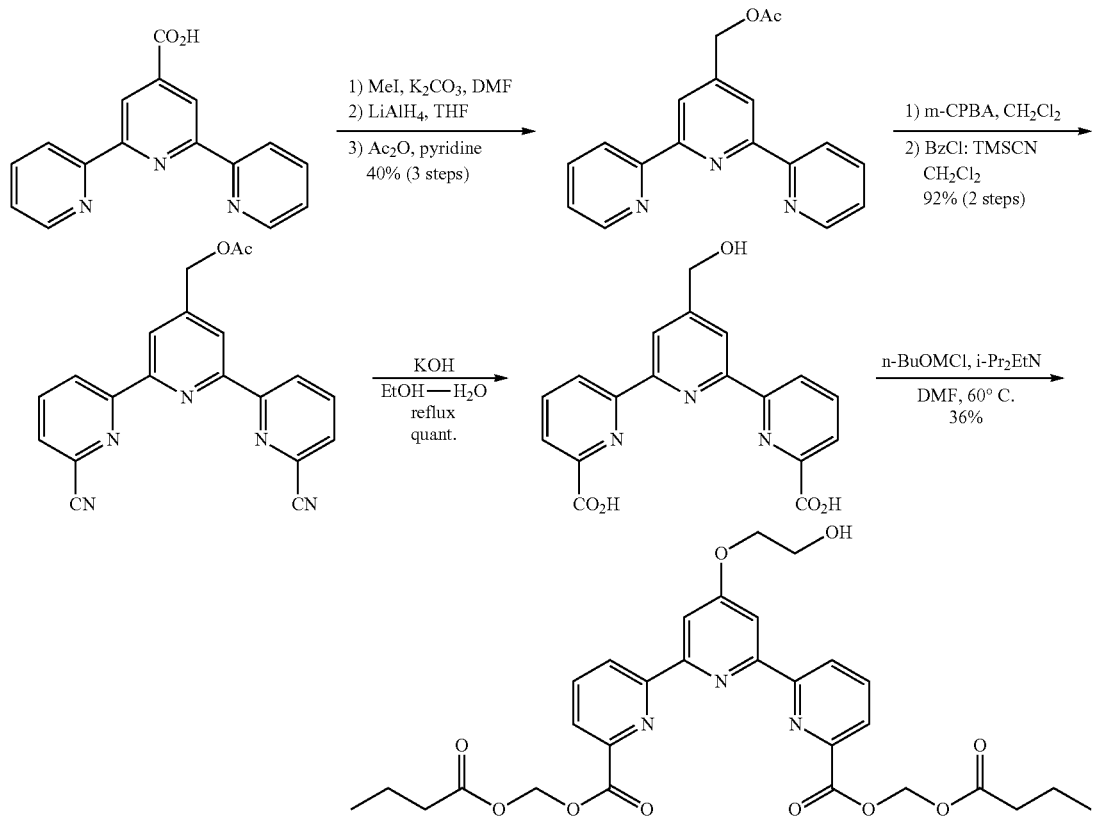

(Step 2)

To a solution of 2,2':6',2''-terpyridine-4'-ylmethyl acetate (88 mg, 0.28 mmol) in dichloromethane (2.8 mL) was added m-chloroperbenzoic acid (170 mg, 75%, 0.74 mmol) at 0° C. After stirring for 19 hr, the mixture was washed with aqueous saturated sodium thiosulfate solution (20 mL), and the aqueous layer was extracted with chloroform (2×20 mL). The combined organic layer was washed with saturated aqueous sodium hydrogen carbonate solution and brine. The organic layer was dried over sodium sulfate, filtered, and concentrated under reduced pressure. The residue was dissolved in dichloromethane (2.8 mL), and benzoylchloride (0.10 mL, 0.86 mol) was added to the obtained solution at room temperature. After stirring for 20 min, trimethylsilyl cyanide (0.11 mL, 0.87 mmol) was added dropwise, and the mixture was stirred at room temperature for 19 hr. The solution was partitioned by adding saturated aqueous sodium hydrogen carbonate solution (5.0 mL), and the aqueous layer was extracted with chloroform (3×5.0 mL). The combined organic layer was washed with brine, dried over sodium sulfate, and concentrated under reduced pressure. The residue was purified by silica gel column chromatography (eluent: chloroform:ethyl acetate=1:0-15:1) to give (6, 6''-dicyano-2,2':6',2''-terpyridine-4'-yl)methyl acetate (92 mg, yield 92%) as a white solid.

$^1$H NMR (500 MHz, CDCl$_3$) δ 2.26 (s, 3H), 5.33 (s, 2H), 7.76 (d, J=7.5 Hz, 2H), 8.02 (t, J=7.5 Hz, 2H), 8.52 (s, 2H), 8.81 (d, J=7.5 Hz, 2H); $^{13}$C NMR (125 MHz, CDCl$_3$) δ 20.9, 64.4, 117.2, 120.7, 124.3, 128.5, 133.4, 138.0, 148.1, 154.0, 157.0, 170.6.

(Step 3)

To a solution of (6, 6''-dicyano-2,2':6',2''-terpyridine-4'-yl)methyl acetate (80 mg, 0.23 mmol) in ethanol (6.9 mL) and distilled water (1.8 mL) was added potassium hydroxide (200 mg, 3.9 mmol). The reaction mixture was heated under reflux for 11 hr, and cooled to room temperature. The pH was adjusted to about 4 with 1N hydrochloric acid, and the precipitate was collected by filtration to give 4'-(hydroxymethyl)-2,2':6',2''-terpyridine-6,6''-dicarboxylic acid as a pale-brown solid. The obtained solid was used for the next reaction without further purification.

$^1$H NMR (500 MHz, d-DMSO) δ 4.77 (s, 2H), 8.12 (d, J=7.5 Hz, 2H), 8.17 (t, J=7.5 Hz, 2H), 8.57 (s, 2H), 8.83 (d, J=7.5 Hz, 2H); $^{13}$C NMR (125 MHz, d-DMSO) 562.0, 124.0, 125.0, 138.8, 148.1, 154.0, 154.6, 155.2, 166.0.

(Step 4)

To a solution of 4'-(hydroxymethyl)-2,2':6',2''-terpyridine-6,6''-dicarboxylic acid (18 mg, 0.05 mmol) in DMF (1.0 mL) were added diisopropylethylamine (0.05 mL, 0.29 mmol) and chloromethylbutyrate (0.03 mL, 0.24 mmol). The reaction mixture was heated to 50° C. After stirring for 15 hr, the mixture was cooled to room temperature, and washed with saturated aqueous ammonium chloride solution (2.0 mL). The aqueous layer was extracted with ethyl acetate (3×5.0 mL). The combined organic layer was washed with brine, dried over magnesium sulfate, filtered, and concentrated under reduced pressure. The residue was purified by silica gel column chromatography (eluent: n-hexane:ethyl acetate=2:1-1:1) to give bis(butyryloxymethyl) 4'-(hydroxymethyl)-2,2':6',2''-terpyridine-6,6''-dicarboxylate (10 mg, yield 36%) as a white wax substance.

$^1$H NMR (500 MHz, CDCl$_3$) δ 0.98 (t, J=7.5 Hz, 6H), 1.71 (sext., J=8.0 Hz, 4H), 2.41 (t, J=7.5 Hz, 4H), 2.45 (brt, J=6.0 Hz, 1H), 4.9 (br. d, J=6.0 Hz, 2H), 6.12 (s, 4H), 8.01 (t, J=7.5 Hz, 2H), 8.17 (dd, J=1.0, 7.5 Hz, 2H), 8.61 (s, 2H), 8.80 (dd, J=1.0, 7.5 Hz, 2H); $^{13}$C NMR (125 MHz, CDCl$_3$) δ 13.5, 18.1, 35.8, 63.9, 80.2, 119.7, 124.9, 125.6, 137.9, 146.5, 152.6, 154.5, 156.5, 163.9, 172.3.

Example 9 bis(acetoxymethyl) 4'-(hydroxymethyl)-2,2':6',2''-terpyridine-6,6''-dicarboxylate

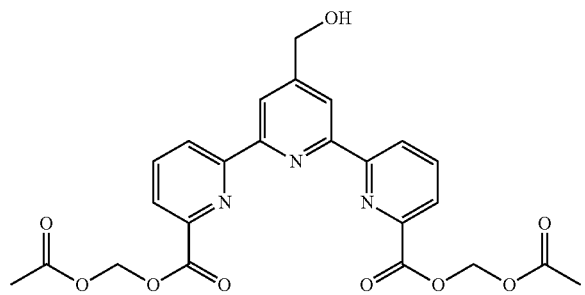 [SMILES: CC(=O)OCOC(=O)c1cccc(-c2cc(CO)cc(-c3cccc(C(=O)OCOC(C)=O)n3)n2)n1]

According to the method described in the above-mentioned Method A, step 3 (0.05 mmol scale), and using 4'-(hydroxymethyl)-2,2':6',2''-terpyridine-6,6''-dicarboxylic acid and acetoxymethylchloride, the reaction was performed. The obtained crude product was purified by silica gel column chromatography (eluent: hexane:ethyl acetate=2:1-1:3) to give the title compound (5.2 mg, yield 20%) as a white solid.

$^1$H NMR (500 MHz, CDCl$_3$) δ 2.18 (s, 6H), 4.96 (brs. 2H), 6.11 (s, 4H), 8.02 (t, J=7.5 Hz, 2H), 8.19 (d, J=7.5 Hz, 2H), 8.62 (s, 2H), 8.82 (d, J=7.5 Hz, 2H); $^{13}$C NMR (125 MHz, CDCl$_3$) δ 20.8, 63.9, 80.2, 119.7, 125.0, 125.7, 137.9, 138.9, 146.5, 154.6, 156.5, 169.6.

Example 10: Cellular Cytotoxicity Measurement Using the Compound of the Present Invention (the Amount of Spontaneous Release Needs to be Monitored when a Time-Resolved Fluorometric Assay (Eu Assay:1) is Performed, the Method Thereof is Indicated Below)

Histiocytoma U937 cells were cultured in 30 mL of RPMI1640 medium under the conditions of 37° C., 5% CO$_2$ overnight, the culture medium (30 mL) was placed in a 50 mL conical tube, and the cell number was counted. After centrifugation at 1700 rpm at 4° C. for 5 min, the supernatant was removed, and the cell pellets were resuspended in RPMI1640 medium at 1×10$^6$ cells/mL. To the cell suspension (1 mL) in a 15 mL conical tube was added 2.5 µL of a compound represented by the formula (I) or a salt thereof (10 mM stock solution) (final concentration: 25 µM), and the mixture was incubated under the conditions of 37° C., 5% CO$_2$ for 15 min. The cells were washed 3 times with 5 mL of RPMI1640 medium, and resuspended in 5 mL of RPMI1640 medium. The cell suspension (2 mL) was placed in a 15 mL conical tube containing 6 mL of RPMI1640 medium to adjust the cell concentration to 5×10$^3$ cells/100 µL. The cell suspension (100 µL) was seeded in 6 wells of a 96 flat bottom plate. 100 µL of RPMI1640 medium was added to wells for determining the amount of spontaneous release, and 90 µL of RPMI1640 medium was added to wells for determining the amount of maximum release. The plates were centrifuged at 500 rpm, room temperature for 2 min and incubated under 37° C., 5% CO$_2$ condition for 30 min. A newly-prepared 0.125% digitonin solution in 19% DMSO (mixed solution of 3 mg digitonin, 0.456 mL DMSO and 1.944 mL $H_2O$) (10 μL) was added to the aforementioned wells for determining the amount of maximum release, mixed well and further incubated for 30 min. After incubation, the cell suspension was mixed well again, and centrifuged at 1700 rpm, room temperature for 2 min. After the centrifugation, the supernatant (25 μL) was carefully transferred into wells containing 250 μL of europium solution in a 96 flat bottom plate, and 200 μL of the solution thereof was placed in a 96-well flat bottom plate.

The plate was allowed to stand for 15 min, and the time-resolved fluorescence was measured by ARVO multiplate reader.

The results of the measurement by the above-mentioned method are shown in the following Table 1.

TABLE 1

| compound | spontaneous release (A) | maximum release (B) | spontaneous release (%) (C) (100 × A/B) | labeled molecule advantage Index (B/C) |
|---|---|---|---|---|
| Example 1 | 6347 | 65576 | 9.7 | 6775 |
| Example 2 | 7085 | 60521 | 11.7 | 5170 |
| Example 3 | 4890 | 69372 | 7 | 9841 |
| Example 4 | 3590 | 43224 | 8.3 | 5204 |
| Example 5 | 6991 | 78831 | 8.9 | 8889 |
| Example 6 | 9538 | 103235 | 9.2 | 11174 |
| Example 7 | 6133 | 63594 | 9.6 | 6594 |
| Example 8 | 14441 | 199608 | 7.2 | 27590 |
| Example 9 | 21343 | 127955 | 16.7 | 7671 |
| BATDA | 14795 | 86785 | 17 | 5091 |

Example 11: Cellular Cytotoxicity Measurement Using the Compound of the Present Invention (Time-Resolved Fluorometric Assay (Eu Assay:1))

(1) Preparation of Target Cell

The cell line HCT-4 cells derived from the cerebrospinal fluid of a human T-lymphotropic virus (HTLV-1)-associated myelopathy patient were cultured overnight in 30 mL of RPMI1640 medium under the conditions of 37° C., 5% $CO_2$ and resuspended in RPIMI1640 medium (20 mL) at 0.24×$10^6$ cells/mL. After centrifugation at 1700 rpm at 4° C. for 5 min, the supernatant was removed, and the cell pellets were resuspended in 4.8 mL of RPMI1640 medium at 1×$10^6$ cells/mL. The cell suspension (1 mL) was placed in each of two 15 mL conical tubes (A-1, A-2).

(2) Preparation of Target Cells

The cell line K562 derived from human chronic leukemia was cultured in 30 mL of RPMI1640 medium overnight under the conditions of 37° C., 5% $CO_2$, seeded in RPIMI1640 medium 20 mL at 4.8×$10^6$ cells, the cell number was counted and adjusted to 0.24×$10^6$ cells/mL. After centrifugation at 1700 rpm at 4° C. for min, the supernatant was removed, and the cells were resuspended in 4.8 ml of RPMI1640 medium at 1×$10^6$ cells/mL. The cell suspension (1 mL) was placed in each of three 15 mL conical tubes (B-1, B-2, B-3) and 2.5 μL of DMSO was added to B-1, and 2.5 μL each of 10 mM compound of Example 8 was added to B-2 and B-3. The mixtures were allowed to stand at 37° C. for 15 min. The cells were washed 3 times with 5 mL of RPMI1640 medium, centrifuged at 1700 rpm at 4° C. for 5 min, and resuspended in 5 mL of RPMI1640 medium. The cell suspension (2 mL) was placed in a 15 mL conical tube containing 6 mL of RPMI1640 medium.

(3) Preparation of Effector Cell

Helper NK cells (60×$10^3$ cells) were suspended in 12 ml of RPMI culture medium, centrifuged at 1700 rpm, 4° C. for 5 min, the supernatant was discarded, and the cells were resuspended in 3 ml of RPMI1640 culture medium.

A serial dilution of cells (3 ml each) was prepared as follows.

Helper NK cell concentration effector cell/target cell ratio 40 2×$10^6$/ml effector cell/target cell ratio 20 1×$10^6$/ml effector cell/target cell ratio 10 5×$10^5$/ml effector cell/target cell ratio 5 2.5×$10^5$/ml effector cell/target cell ratio 2.5 1.25×$10^4$/ml effector cell/target cell ratio 1.25 6.25×$10^3$/ml effector cell/target cell ratio 0.625 3.125×$10^3$/ml effector cell/target cell ratio 0 0/ml (Cell concentration):

The helper NK cell suspensions at the above-mentioned concentrations (100 μL each), and RPIM1640 culture medium (100 μL) were added to a 96 flat bottom plate to determine the amount of spontaneous release, and those and RPIM culture medium (90 μL) were added to a 96 flat bottom plate to determine the amount of maximum release. To the 96-well plate were added 100 μL each of the HCT-4 cell solution and K562 cell solution.

The configuration of the above-mentioned 96-well plates is as shown in FIG. 1. The plates were centrifuged at 500 rpm, room temperature for 2 min and incubated at 37° C. for 20 min. A 0.125% digitonin solution in 19% DMSO (mixed solution of 3 mg digitonin, 0.456 mL DMSO and 1.944 mL $H_2O$) was newly prepared and 10 μL thereof was added to the aforementioned wells for determining the amount of maximum release and mixed well, and the plate was further incubated for 20 min. After incubation, the cell suspension was mixed well again, and centrifuged at 1700 rpm, room temperature for 2 min. After centrifugation, the supernatant (25 μL) was carefully removed, placed in a 96 flat bottom plate containing 250 μL of europium solution, and 200 μL of the solution thereof was placed in a 96-well Nunc plate. The plate was allowed to stand for 15 min, and the time-resolved fluorescence was measured by ARVO multiplate reader.

Figure 3:
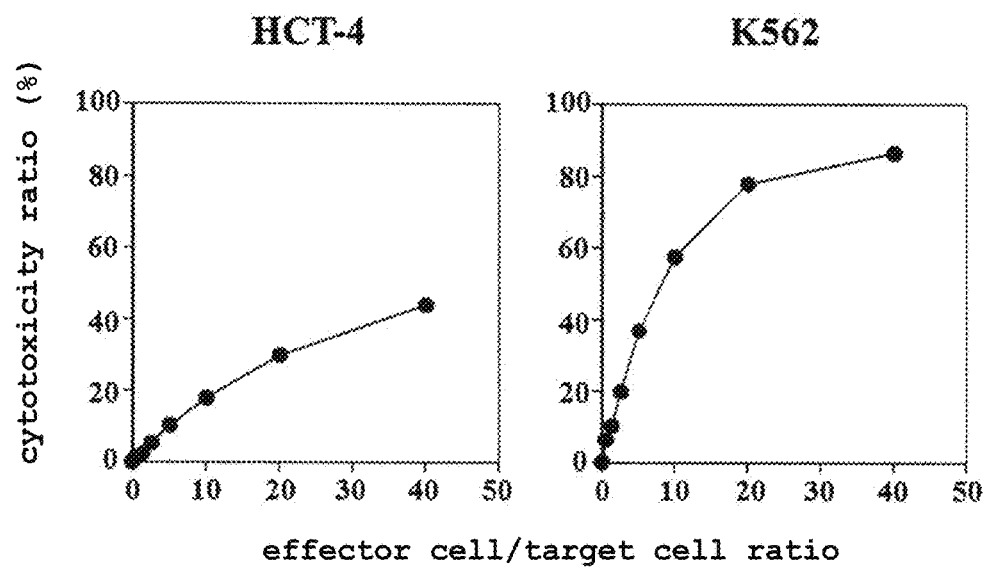
FIG. 3 shows the results of cellular cytotoxicity measurement using the compound of the present invention (Example 8).

The results of measurement by the above-mentioned method are shown in FIG. 2 and FIG. 3.

Therefrom it was shown that the cellular cytotoxicity of effector cells can be measured.

INDUSTRIAL APPLICABILITY

The compound of the present invention is useful as a reagent for measuring cellular cytotoxicity or cell proliferation capacity. Also, using the reagent, cellular cytotoxicity and cell proliferation capacity can be measured accurately with high reproducibility, conveniently and rapidly.

This application is based on a patent application No. 2014-073475 filed in Japan (filing date: Mar. 31, 2014), the contents of which are incorporated in full herein.

The invention claimed is:
1. A compound represented by the formula (I):

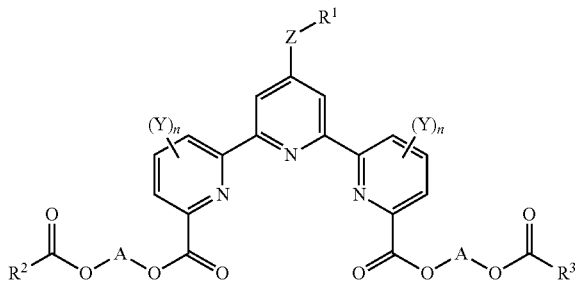

wherein
R¹ is $C_{1-6}$ alkyl optionally substituted by 1 to 3 substituents selected from (1) a hydroxy group, (2) a formyl group, (3) a $C_{1-6}$ alkyl-aminocarbonyl group, and (4) a hydroxy-$C_{1-6}$ alkoxy group,
R² and R³ are each an optionally substituted hydrocarbon group, or an optionally substituted heterocyclic group,
Y is not present,
n is 0,
Z is a single bond or —O—, and
A is methylene,
or a salt thereof.

2. The compound according to claim 1, wherein R² and R³ are $C_{1-6}$ alkyl groups, or a salt thereof.

3. The compound according to claim 1, wherein R¹ is $C_{1-6}$ alkyl substituted by 1 to 3 substituents selected from (1) a hydroxy group, (2) a formyl group, (3) a $C_{1-6}$ alkyl-aminocarbonyl group and (4) a hydroxy-$C_{1-6}$ alkoxy group, or a salt thereof.

4. The compound according to claim 3, wherein Z is a single bond, or a salt thereof.

5. The compound according to claim 3, wherein Z is —O—, or a salt thereof.

6. The compound according to claim 1, wherein Z is a single bond, or a salt thereof.

7. The compound according to claim 1, wherein Z is —O—, or a salt thereof.

8. The compound according to claim 1, wherein R¹ is $C_{1-6}$ alkyl substituted by a hydroxy group, or a salt thereof.

9. The compound according to claim 8, wherein Z is a single bond, or a salt thereof.

10. The compound according to claim 8, wherein Z is —O—, or a salt thereof.

11. An organic complex-forming agent comprising the compound according to claim 1, or a salt thereof.

12. A reagent for viable cell number measurement, comprising the compound according to claim 1, or a salt thereof.

13. The reagent according to claim 12, which is a reagent for cytotoxicity measurement.

14. The reagent according to claim 12, which is a reagent for cell proliferation capacity measurement.

15. A method of measuring cytotoxicity, comprising
a step of mixing the compound according to claim 1 or a salt thereof and a cell, and
a step of forming a complex with a lanthanoid element and measuring fluorescence.

16. The method according to claim 15, wherein a surfactant is added before forming the complex with a lanthanoid element.

* * * * *